United States Patent
Hibbs et al.

(10) Patent No.: US 7,622,934 B2
(45) Date of Patent: Nov. 24, 2009

(54) METHOD AND APPARATUS FOR SENSING A TIME VARYING CURRENT PASSING THROUGH AN ION CHANNEL

(75) Inventors: Andrew D. Hibbs, La Jolla, CA (US); Regina E. Dugan, Rockville, MD (US)

(73) Assignee: Electronic Bio Sciences, LLC, San Diego, CA (US)

(*) Notice: Subject to any disclaimer, the term of this patent is extended or adjusted under 35 U.S.C. 154(b) by 236 days.

(21) Appl. No.: 11/658,094

(22) PCT Filed: Jul. 22, 2005

(86) PCT No.: PCT/US2005/026181

§ 371 (c)(1),
(2), (4) Date: Jan. 22, 2007

(87) PCT Pub. No.: WO2006/012571

PCT Pub. Date: Feb. 2, 2006

(65) Prior Publication Data

US 2008/0094076 A1    Apr. 24, 2008

Related U.S. Application Data

(60) Provisional application No. 60/590,351, filed on Jul. 23, 2004.

(51) Int. Cl.
*G01R 27/26* (2006.01)

(52) U.S. Cl. .................... 324/686; 324/658; 435/6; 204/400

(58) Field of Classification Search ............... 324/686, 324/459, 439, 445, 446, 658; 435/6; 204/400
See application file for complete search history.

(56) References Cited

U.S. PATENT DOCUMENTS

| | | |
|---|---|---|
| 4,055,799 A | 10/1977 | Coster et al. |
| 5,368,712 A | 11/1994 | Tomich et al. |
| 5,503,744 A | 4/1996 | Ikematsu et al. |
| 5,516,890 A | 5/1996 | Tomich et al. |
| 5,795,782 A | 8/1998 | Church et al. |
| 6,210,551 B1 | 4/2001 | Osman et al. |
| 6,355,420 B1 | 3/2002 | Chan |
| 6,379,916 B1 | 4/2002 | Meyer |
| 6,426,231 B1 | 7/2002 | Bayley et al. |
| 6,570,196 B1 | 5/2003 | Fromherz et al. |
| 6,776,896 B1 | 8/2004 | Osipchuk |
| 6,787,368 B1 | 9/2004 | Wong et al. |
| 2002/0045159 A1 | 4/2002 | Maher et al. |
| 2002/0053915 A1 | 5/2002 | Weaver et al. |
| 2002/0182627 A1* | 12/2002 | Wang et al. ............ 435/6 |
| 2003/0054333 A1 | 3/2003 | Hickman et al. |
| 2003/0062657 A1 | 4/2003 | Parameswaran et al. |

(Continued)

FOREIGN PATENT DOCUMENTS

WO        WO 03/095669        11/2003

*Primary Examiner*—Vincent Q Nguyen
(74) *Attorney, Agent, or Firm*—Diederiks & Whitelaw, PLC (57) ABSTRACT

A capacitive sensing system is used to measure a time-varying ion current through a channel, such as an ion channel or protein pore. Such a capacitive system does not suffer problems of electrode corrosion and, when used with methods to control a build up of ion concentration, allows the use of measurement volumes around the channel with dimensions on a scale of nanometers.

27 Claims, 3 Drawing Sheets

U.S. PATENT DOCUMENTS

| | | |
|---|---|---|
| 2003/0215881 A1 | 11/2003 | Bayley et al. |
| 2003/0222050 A1* | 12/2003 | Dugas et al. .................. 216/2 |
| 2003/0231531 A1 | 12/2003 | Baxter et al. |
| 2004/0005696 A1 | 1/2004 | Vestergaard et al. |
| 2004/0020773 A1 | 2/2004 | Thomsen et al. |
| 2004/0038421 A1 | 2/2004 | Cuppoletti |
| 2004/0106126 A1* | 6/2004 | Fendler ....................... 435/6 |
| 2004/0214312 A1 | 10/2004 | Tyvoll et al. |
| 2004/0251145 A1 | 12/2004 | Robertson |
| 2004/0262636 A1 | 12/2004 | Yang et al. |
| 2005/0004442 A1 | 1/2005 | Ozaki et al. |
| 2005/0053961 A1 | 3/2005 | Akeson et al. |
| 2005/0098841 A1* | 5/2005 | Barth ......................... 257/414 |
| 2005/0112557 A1 | 5/2005 | Liu et al. |

* cited by examiner

METHOD AND APPARATUS FOR SENSING A TIME VARYING CURRENT PASSING THROUGH AN ION CHANNEL

CROSS-REFERENCE TO RELATED APPLICATION

The present application represents a National Stage application of PCT/US2005/026181 filed Jul. 22, 2005 entitled "Method and Apparatus For Sensing a Time Varying Current Passing Through an Ion Channel", and claims the benefit of U.S. Provisional Patent Application Ser. No. 60/590,351 filed Jul. 23, 2004 entitled "Sensing Means For Ion Channels and Protein Pores."

This application claims the benefit of U.S. Provisional Patent Application Ser. No. 60/590,351 filed Jul. 23, 2004.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract A9550-05-C0050 awarded by the U.S. Air Force Office of Scientific Research.

BACKGROUND OF THE INVENTION

The present invention pertains to the art of electrical sensing devices and, more particularly, to a method and apparatus for sensing a time varying electrical current passing through an ion channel located in a membrane. A membrane typically surrounds biologic cells, with the membrane having ion channels located therein. These ion channels are made of protein structures that regulate the passage of various ions into and out of the cell. These ion channels are important to study due to their wide variety of biological functions. In the past, such ion channels were studied by clamping a portion or patch of a cell membrane and measuring changes in its electrical properties when the membrane and ion channels were exposed to various analytes which altered the ion channel's behavior. Unfortunately, there are great difficulties in positioning a cell for such measurement. In order to make ion channel studies more efficient, people have modeled the cell membrane by forming a lipid bilayer membrane and inserting therein proteins that act as ion channels. Such an artificial membrane may then be used in experiments rather than an actual cell membrane.

In a manner known in the art, measurements of ionic current passing through an ion channel or protein pore, nanochannel or other aperture of a membrane maintained in an electrolyte have been made using first and second electrodes in resistive electrical contact with the electrolyte. The first electrode is maintained in a first or bath volume of electrolyte, while the second electrode is maintained in a second or sensing volume of electrolyte. A voltage differential is maintained between the first and second electrodes establishing an electrical field. At an interface between the first (resistive) electrode and an ionic solution, an oxidation-reduction (redox) reaction must occur for a charge to transfer between the first electrode and the solution. In the oxidation part of the reaction, atoms of the first electrode enter the solution as cations. The cations move through the solution under the influence of diffusion and the electrical field and are deposited at the second electrode as the cations are reduced.

The interaction between the resistive electrode and the solution produces a concentration gradient of the ions in solution near the surface of the first electrode. The gradient causes a half-cell potential to be established between the first electrode and the bulk of the electrolyte. If a current flows, these potentials can be altered causing an over-voltage to appear. The over-voltage results from an alteration in a charge distribution of the solution in contact with the first and second electrodes, creating a polarization effect. The resulting charge distribution can cause a significant measurement artifact if either the first or second electrodes move relative to the solution for any reason.

In order to minimize these well-known problems with resistive electrodes, prior measurement apparatuses have positioned the measurement volume of interest away from a region of variable concentration around the electrodes. In suspended membrane geometry, volumes having dimensions in the order of 1 cm×1 cm×1 cm are typically utilized on either side of the membrane. A wire electrode is immersed in each volume at a distance in the order of millimeters from an active area of the channel (or pore etc.). At this distance scale concentration gradient effects are negligible. However, it should be readily apparent that as the scale of the measurement apparatus is reduced, it becomes increasingly difficult to spatially separate the area with concentration gradients from the active region of interest. Indeed, in the limiting case of a supported membrane, a geometry involving a membrane deposited directly on an electrode, or separated from it by a thin (1 nm) layer, it has not yet proven possible to record a signal from a single channel.

In addition, as the overall scale of the apparatus is reduced, the volume is also reduced and the duration over which the second electrode can maintain an ionic current before the electrode is fully dissolved is reduced accordingly. Traditional patch clamp type experiments are limited to approximately one hour due to limitations in the lifetime of various aspects of the system. However, electrode degradation is not usually a limiting factor. In any case, for new applications that seek to study long-term effects and for systems with micrometer or nanometer scale electrodes, the lifetime of a resistively coupled electrode could be a limiting factor. A similar problem occurs due to the build up of ions from solution. If the region around the electrode is limited to nanometers by, for example, the presence of a supported membrane, then the deposition of even a nanometer of atoms from solution can present a significant problem.

A capacitive electrode does not suffer redox and concentration related problems as the electrode is insulated from the solution. Therefore, no ionic reaction occurs at the electrode. However, the capacitive electrode does produce a potential in the electrolyte. A capacitive electrode couples to the electrolyte by virtue of its mutual capacitance to the electrolyte. This potential induces ions to flow in the body of the electrolyte just as if a resistive electrode coupled the potential. An oscillating ionic current is maintained in the electrolyte by a displacement current induced in insulation around the capacitive electrode. In an identical manner, a capacitive electrode can also be used to measure the potential of an ionic fluid.

Despite these benefits, capacitive electrodes have not previously been used to measure potentials or currents in electrolytes. The reason is that existing biopotential electrodes have been adequate for experimental scale geometries utilized to date and have the benefit of being DC coupled. In addition, although the benefit of capacitive electrodes increases with reduced apparatus size, capacitive electrodes themselves become more difficult to use. That is, as the electrodes are made smaller, the capacitance of the electrode is reduced to a very small level. For example, for a 10 μm×10 μm electrode that might be used in a chip scale sensor, the capacitance of the electrode is in the order of less than 1 pF. At low frequency, a capacitance in the order of 1 pF represents very high impedance. Coupling an amplifier efficiently to such a high impedance source while maintaining low input noise levels and removing low frequency drift is traditionally a difficult problem.

New ways to couple to a very small, purely capacitive source have been taught by U.S. Pat. No. 6,686,800 B2. New systems that utilize such capacitive sensing to measure electrophysiological signals such as the human electrocardiogram (ECG) and electroencephalogram (EEG) are known in the art. In these cases, the capacitance of the region used to sense the potential was in the range of 10 pF to less than 1 pF. Other prior art arrangements used a capacitive method to measure the potential of a cell. The method employed an in situ transistor with the cell being deposited directly on a gate of a transistor. The internal potential of the cell and the potential of a cleft region, i.e., a small region of fluid between the cell and the upper surface of the transistor, were coupled into the transistor to produce a measurable signal.

In prior measurement arrangements that employ low-capacitance sensors, the variable of interest was the electric potential produced within a heart, brain, or other cell. In the case of the cell, the potential of the cleft region between the cell outer surface and the point of measurement was, in most cases, found to obscure and dominate the cell potential. The potential of the cleft region is determined by a combination of capacitive coupling to the internal potential of the cell, ionic current that flows through channels in a portion of the cell that faces the cleft region, and a resistive coupling through the electrolyte in the cleft region to the bath that maintains the cell. Owing to variations in spacing the cell from the electrode (i.e. the height of the cleft region) and in the local properties of the cell membrane, there is considerable, uncontrollable variation in the coupling of the cell potential to the transistor.

As a way to better control the cleft region, the prior art teaches attaching a lipid vesicle to a transistor instead of attaching the cell to the transistor. Because the lipid vesicle lacks an outer coating of proteins and oligo-saccharides, found around most cells, the lipid vesicle forms a cleft region having a lower, and a more reproducible height. However, as for the cell, there is a continuous fluid path from the electrolyte in the cleft region to the reservoir that contains the bulk of the electrolyte. Accordingly, there is always a conducting path from the cleft region to the electrode in the reservoir. The resistance of the conducting path is not a property of the membrane, but a difficult-to-control variable that depends on proper adhesion of the lipid vesicle to the transistor.

Other capacitive sensing configurations teach depositing a black lipid membrane containing gramicidin channels over an insulating groove provided in a silicon substrate. A linear array of transistors is fabricated at a bottom surface of the insulating groove. Electrodes are fabricated within the insulating groove at each end of the linear array in order to drive a current along a length of the array. A change in density of open channels was determined by a change in a voltage profile along the length of the groove.

Based on the above, there still exists a need for sensing time varying current passing through a membrane. More specifically, there exists a need for an apparatus that establishes general measurement geometry and associated electronic biasing techniques to enable a capacitive sensor to measure an ionic current passed by an ion channel or protein pore of a membrane.

SUMMARY OF THE INVENTION

The present invention is directed to a sensing apparatus or system for sensing a time varying current passing through a membrane. In accordance with the invention, the system includes first and second volumes that are filled with an electrolyte and separated by a membrane. The first volume or bath is large and can be common to multiple membranes. The second or sensing volume is generally smaller than the first volume. In the case that multiple membranes are coupled to the same bath, each sensing volume serves to localize measurement to a specific membrane of interest. An analyte(s) of interest is introduced into the bath.

The sensing system further includes a first electrode positioned in the bath and a second electrode positioned in the sensing volume. Establishing a potential difference between the first and second electrodes produces an electric field. The electric field causes an ionic current to flow from the bath to the sensing volume. A third electrode, electrically coupled with the sensing volume, senses the ionic current. Preferably, the third electrode is a capacitive electrode connected to a high impedance circuit. In accordance with one aspect of the invention, the second and third electrodes could be a single unit so long as additional circuitry is provided to isolate the electric field from the ionic current.

With this arrangement, the ionic current flowing through the membrane is measured. More specifically, within the membrane are one or more ion channels and/or protein pores which can be engineered or otherwise modified as desired for a specific measurement application. For convenience, an ion channel, protein pore, nanochannel, micro aperture, or any functionally similar structure that enables ions to traverse the membrane, is denoted as a channel. A fundamental parameter of interest is a time varying ionic current that passes across the channel from the bath to the sensing volume. However, other physical variables such as leakage current of the membrane could, in some cases, be a parameter of interest and the invention applies to all properties of the channel or membrane that can be measured capacitively.

Because of its improved sensitivity with a reduced volume, capacitive sensing allows the use of a reduced ionic current. This enables implementation with the use of a lower bias voltage or the use of lower concentration electrolytes. In the prior art, electrolyte conductivity is traditionally set at the high end of acceptable levels in order to maximize the ionic current. In some cases, it would be desirable to reduce the electrolyte concentration. However, this is not typically done in the prior art due to signal to noise ratio (SNR) considerations.

A particular application of the invention is to measure discrete conductivity states in channels. These states change stochastically in the presence of analytes in a manner that allows separate determination of concentration and species. Another application of the invention is to measure channel current when conductivity is simply determined by a blocking effect produced by the presence of an analyte in an internal flow region of the channel. Such a measurement is the capacitive analog of the resistive pulse technique that is the basis of the Coulter counter. The capacitive technique has the same general benefits when going to smaller length scales as it does for stochastic sensing.

A benefit of the capacitive method is that, because the impedances of the electrodes and driving voltage circuitry are so high as compared to the electrolyte, electrolyte resistance does not contribute to system noise over a range of typical system values. In some patch clamp measurements, pipette access resistance sets a minimum detectable signal level. Thus, for some experimental situations, the present invention offers higher sensitivity than possible in prior art patch clamp methods.

In the prior art patch clamp method that is the standard for present measurements, the channel is biased at a fixed voltage that is maintained by feedback if necessary (i.e., voltage clamping). In the case of the present invention, DC potential can be measured directly by resistive electrodes if these are used. In the case of a bias voltage, such electrodes are connected to a very high impedance circuit to prevent current flow that could short the potential of the sensing volume.

The present invention preferably only utilizes capacitive coupling to the electrolyte. In this case, the DC potential is deduced from net ionic current that flows into the sensing volume. The required DC voltage can be maintained across the channel by driving the bath voltage to a given potential difference from the measured sensing volume potential. Alternatively, a desired potential difference could be created by allowing a specified amount of net charge to build up in the sensing volume and to bias the subsequent ion current to have zero average deviation about this net value. The output waveform can then be calculated based on capacitive coupling of the bias voltage to the bath and sensing volume.

A benefit of capacitive sensing in the measurement configuration described by the invention is that the resulting system noise is, in many configurations, less dependent on the seal resistance between the membrane and the rest of the system than is the traditional patch clamp method. In particular, relatively low values of the seal resistance (<100 MΩ) appear in general to have less of an overall effect on the system noise than the same seal resistance would for the patch clamp method.

By virtue of their very nature, capacitive sensors have a further benefit for measuring ionic currents in small devices. To measure the variation in ionic current flowing in an ion channel or protein pore, a means must be provided to convert the current to a voltage. This is easily and naturally achieved by the fact that, as an ionic current flows into a confined volume, a net electrostatic charge builds up as the ion current accumulates. This build up charge leads to an increase in the electric potential in a manner analogous to the rise in potential due to the build up of charge during electron flow into a capacitor. In addition to great simplicity, this effect has the very desirable property that, as the volume in question is reduced in size, its capacitance decreases and, as a result, the voltage produced by a given net charge increases.

Conventional resistive contact electrodes do not measure this build up of potential because, by their very nature, such electrodes provide an electron current which combines with and neutralizes the ions that comprise the current as part of the redox reaction. However, if the current flows for too long a time, the voltage of the sensing volume may increase to approximately equal the voltage that is applied across the membrane to drive the ionic current. Accordingly, the waveform of the driving voltage must be arranged to prevent the build up of unacceptable voltage differences.

Additional objects, features and advantages of the present invention will become more readily apparent from the following detailed description of preferred embodiments when taken in conjunction with the drawings, wherein like reference numerals refer to corresponding parts in the several views.

DETAILED DESCRIPTION OF THE PREFERRED EMBODIMENTS

Figure 1:
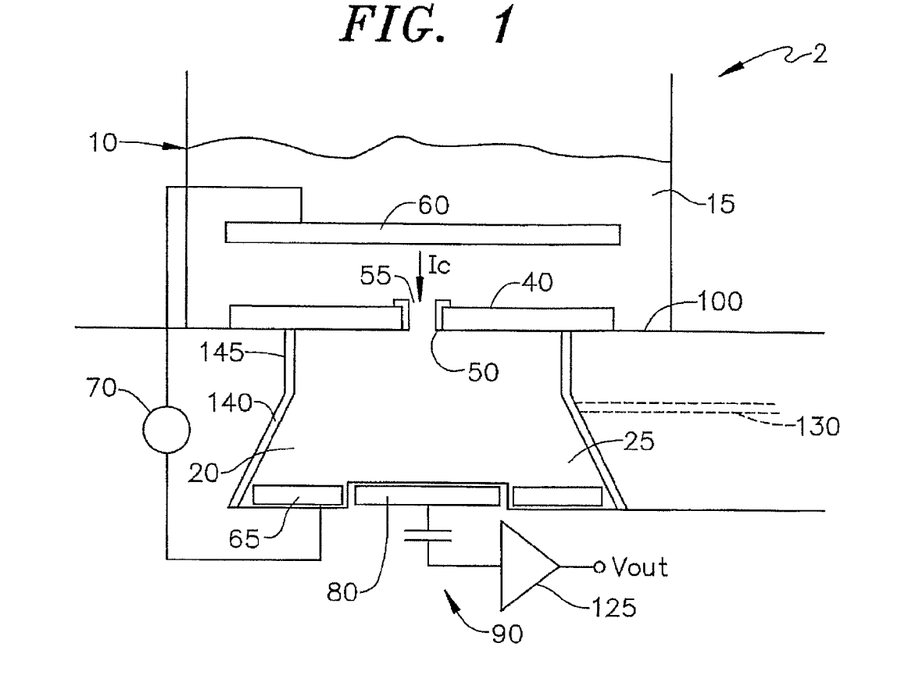
FIG. 1 is a schematic representation of a sensing system constructed in accordance with the present invention.

With initial reference to FIG. 1, a sensing apparatus or system constructed in accordance with the invention is generally indicated at 2. Sensing system 2 includes a first volume or bath 10 within which is provided a first electrolyte 15, and a second or sensing volume 20 provided with a second electrolyte 25. Sensing volume 20 is typically smaller than bath 10. However, it should be noted that this is not a necessary requirement. As shown, membrane 40 separates bath 10 and sensing volume 20. Membrane 40 includes one or more channels, indicated generally at 50, which can be engineered or otherwise modified as desired for a specific measurement application. For convenience, we simply denote an ion channel, protein pore, nanochannel, micro aperture, or any functionally similar structure that enables ions to traverse the membrane, as channel 50. In any event, membrane 40 could be formed from a bilipid, liquid film or a solid material such as polycarbonate or polyimide.

As will be discussed more fully below, a fundamental parameter of interest is a time-varying ionic current $I_c$ that passes across channel 50 from bath 10 to sensing volume 20. However, other physical variables, such as a leakage current of membrane 40, could be the parameters of interest, and the invention applies to all properties of channel 50 or membrane 40 that can be measured capacitively. In addition, the change in current due to a blocking effect produced by the presence of an analyte(s) 55 can be measured.

In accordance with the invention, sensing system 2 includes a first electrode 60 positioned in bath 10 and a second electrode 65 that is positioned in sensing volume 20. A voltage source 70 applies a potential difference or driving potential across first and second electrodes 60 and 65 to establish an ionic current ($I_c$) through channel 50. A third or capacitive sensing electrode 80 is electrically coupled to sensing volume 20 to sense a potential of electrolyte 25. Preferably, capacitive sensing electrode 80 is connected to a high-impedance circuit 90. Of course, it should be understood that second electrode 65 and capacitive sensing electrode 80 can be an integral unit so long as a circuit (not shown) is provided which can isolate the driving potential from high-impedance circuit 90.

While electrodes 60 and 65 may be either resistive or capacitive in nature, preferably electrodes 60 and 65 are capacitively coupled to electrolytes 15 and 25, respectively, and an AC voltage is applied at voltage source 70. Preferably, the capacitance of electrodes 60 and 65 is in the order of 1 pF. When driven at 100 Hz, the impedance of electrodes 60 and 65 is in the order of 1 GΩ, which is much higher than the impedance of electrolyte 25. The difference in impedance results in a negligible electric field in electrolytes 15 and 25. However, the impedance of each of electrodes 60 and 65 is comparable to the impedance of channel 50. Accordingly, even though there is a negligible electric field in electrolytes 15 and 25, a significant fraction of the applied voltage is developed across channel 50. For example, for 1 pF electrodes with a 100 Hz applied AC voltage, 16% of the applied voltage is developed across a 1 GΩ channel 50 in membrane 40 having a capacitance of approximately 1 pF. Of course, the fact that there is a negligible electric field in electrolytes 15 and 25 is not a concern because, owing to the low average velocity of ions in biological electrolytes at the voltage levels applied, the arrival of ions at channel 50 is controlled by diffusion and not bulk flow.

As noted above, the voltage for driving ion current ($I_c$) could be applied by conventional resistive electrodes, e.g. electrode 60 and 65. In this case, a separate capacitive electrode, e.g. capacitive sensing electrode 80, is used to sense the potential of electrolyte 25 in sensing volume 20. If electrode 65 is a resistive type, then the circuit which is employed to apply voltage 70 to drive ion current ($I_c$) must have a high impedance level, i.e., the impedance level must be sufficient to prevent shorting of channel 50.

Figure 2:
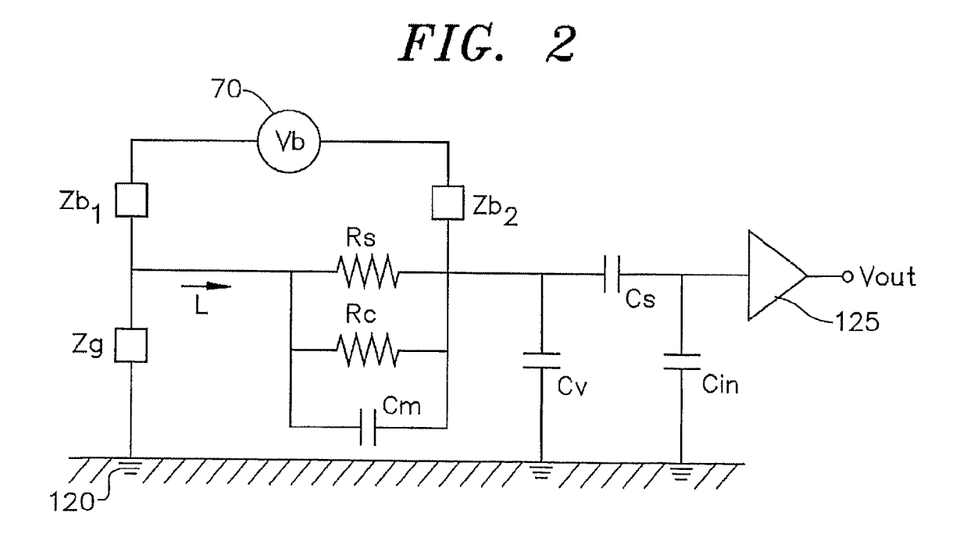
FIG. 2 is a schematic representation of the sensing system of FIG. 1 depicted as an electrical circuit.

A circuit diagram representing the present invention is shown schematically in FIG. 2. Capacitance Cm and resistance Rs that couple sensing volume 20 and bath 10 represent membrane 40. $R_s$ represents all sources of shunt resistance, including a seal (not labeled) present between membrane 40 and a substrate 100 (FIG. 1), defects in membrane 40, and defects in sealing channel 50 to membrane 40. Channel 50 is represented by a resistance $R_c$, a time-varying resistance that varies between approximately 1 GΩ and several hundred GΩ depending on the nature of channel 50. In some cases, the variation may only constitute modulation of the current $I_c$ by a factor of approximately 30%. In addition, channel 50 may have more than two discrete conduction states.

Capacitive sensing electrode 80 is represented by a capacitance $C_s$ to electrolyte 25 in sensing volume 20. In general, capacitive sensing electrode 80 includes a resistance in parallel (not shown) with $C_s$ to represent that no material is a perfect electrical insulator. However, sensing system 2 is predominantly capacitive, with negligible contribution from resistive conduction. Thus, the resistance is not shown. That is, a particular benefit of employing capacitive electrodes is that the impedance of the electrodes and driving voltage circuitry are so high as compared to electrolytes 15 and 25 that the electrolyte resistance does not contribute to system noise over a range of typical system values. This can produce a high sensitivity level that allows for the measurement of discrete conductivity states of channel 50. The conductivity states change stochastically in the presence of analyte 55 so as to allow separate determination of concentration and species. A biasing voltage for driving ionic current ($I_c$) is denoted $V_b$ and is connected to electrolytes 15 and 25 by impedances $Zb_1$ and $Zb_2$. As discussed above, capacitive or resistive electrodes can implement the impedances.

Electrolyte 15 is connected to a circuit ground point 120 through impedance $Z_g$ which can be implemented by either a capacitive or resistive electrode to the electrolyte or via the free-space capacitance of voltage circuit 70 or some combination thereof. Capacitive sensing electrode 80 is connected to circuit ground point 120 through input capacitance $C_{in}$ portion of a readout circuit 125. Readout circuit 125 also includes an input resistance (not shown) relative to ground 120. In any case, the input resistance is preferably established to have a negligible effect at the particular frequencies of interest. In cases wherein the resistance does have a noticeable effect, the resistance can be taken into account in the equivalent circuit. The capacitance of sensing volume 20 to ground is $C_v$. It is important to minimize this capacitance to prevent shunting of the signal to ground point 120. In the cases that sensing volume 20 includes a fluid path 130 to allow filling sensing volume 20 with electrolyte 25, the impedance of fluid path 130 to ground must also be controlled to prevent shorting of the potential of bath 10.

When an ionic current $I_c$ flows into sensing volume 20, the voltage of electrolyte 25 increases in a manner similar to that of a simple capacitor in an electrical sense. Because of the relatively high conductivity, electrolyte 25 is of uniform potential and voltage appears across membrane 40, the capacitance coupling between capacitive sensing electrode 80 and electrolyte 25, readout circuit 125, and insulation 140 on walls 145 of sensing volume 20. As discussed above, a benefit of the capacitive method of measuring ionic current ($I_c$) is that, as sensing volume 20 is reduced, a magnitude of the voltage produced by a given ion current $I_c$ increases. Thus, sensing volume 20 could have an overall thickness of less than approximately 1 mm, and as thin as 1 μ or even 10 nm. For example, while a 100 μm×100 μm×100 μm sensing volume 20 with a given layer of insulation 140 may have a capacitance of order 10 pF, a volume 10 μm×10 μm×1 μm made in the same way would have a capacitance of order 0.1 pF.

Figure 3:
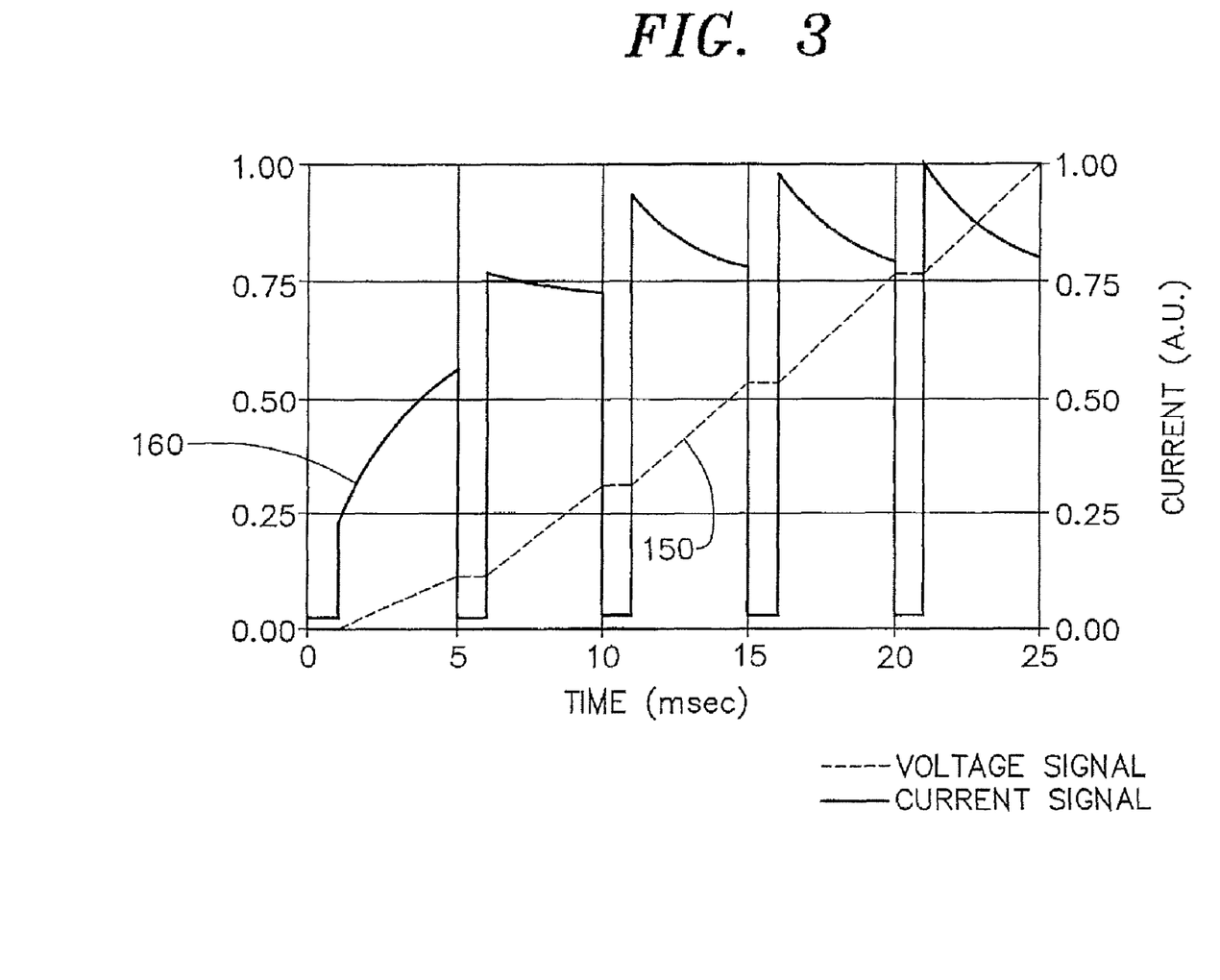
FIG. 3 is a graphic representation of a time varying measured voltage and amplifier input current corresponding to a channel switching between 1 GΩ and 300 GΩ produced with the sensing system of the present invention.

To illustrate the general operation, the output voltage 150 as a function of time of readout circuit 125 for channel 50 that switches between states of 1 GΩ and 300 GΩ is shown in FIG. 3. For reference purposes with a traditional patch clamp current measurement the current 160 that corresponds to voltage 150 is also shown in FIG. 3. The applied voltage from voltage source 70 is a square wave with zero average value with a duration greater and the 25 msec interval shown in FIG. 3. A driving voltage waveform can be of any form, preferably having a zero average value and a maximum total current flowing in any time interval that is insufficient to cause an undesirable voltage to build up in sensing volume 20. Also, the amplitude of the voltage waveform can be adjusted to offset a voltage build up in the sensing volume 20. If the conductivity of channel 50 is asymmetric with respect to a direction of flow, the driving voltage waveform can be adjusted to compensate to produce a zero average voltage in sensing volume 20. Alternatively, a DC or quasi DC potential can be maintained across channel 50 for short periods of time, e.g. approximately 10-20 seconds, by applying a driving current waveform that has a net continually increasing value (e.g. an AC waveform plus a ramp) over the desired time interval. Preferably, the average voltage of sensing volume 20 is monitored in real time and the driving waveform controlled by feedback. The effect of time variation of the bias voltage can be removed by taking a ratio of the signal and the drive voltage, or by some more complex method, such as correlating the drive voltage with the output.

In further accordance with the invention, driving voltage 150 is varied in order to maximize overall performance. That is, driving voltage 150 is maintained at a relatively low level in order to minimize ionic current $I_c$. Current minimization has the benefit of preserving electrode lifetime when conventional resistive electrodes are employed and improves measurement fidelity by minimizing the number of ions in channel 50. When a suspected change in channel conductivity occurs, driving voltage 150 is increased to a higher level in order to improve the signal to noise ratio (SNR) of the measurement.

It should be noted that transit time of an ion within channel 50 is dominated by the ion's mean free path in solution. A molecule executing a random walk through channel 50 will traverse channel 50 in a time of approximately 1 ns. Thus the applied voltage 150 could, in theory, be switched at very high rates if necessary, without affecting the dynamics of the ions within channel 50.

Figure 4:
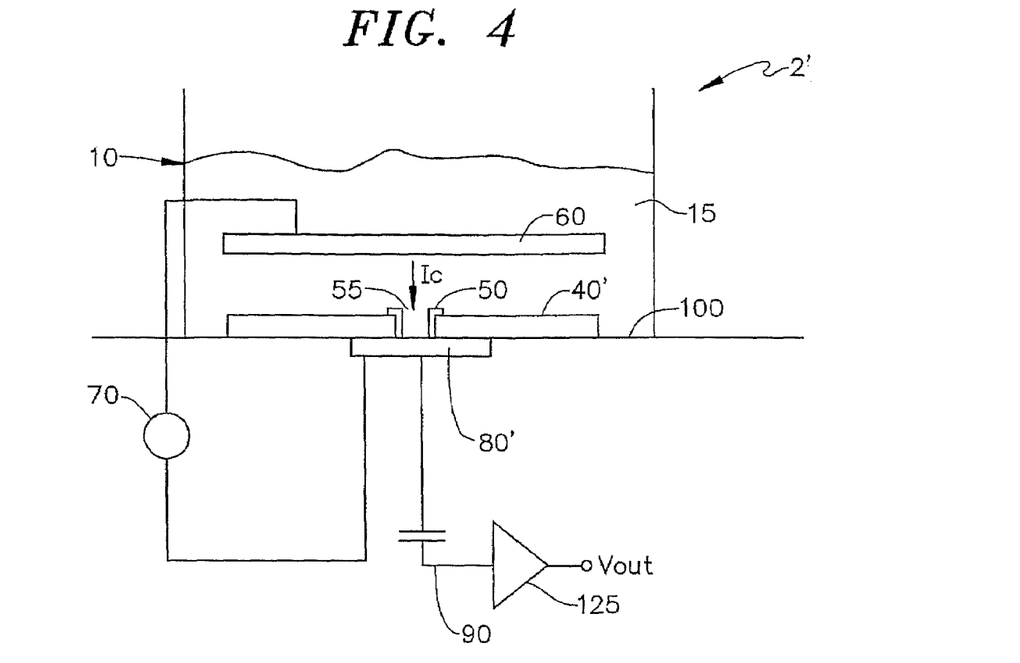
FIG. 4 is a schematic representation of a sensing system constructed in accordance with a second embodiment of the present invention.

In accordance with a second embodiment of the present invention which is illustrated in FIG. 4 and functionally similar to sensing system 2 described above, a sensing system 2 includes a membrane 40' located directly on a capacitive sensing electrode 80' and substrate 100. This geometry is referred to as a supported Membrane, whereas membrane 40, shown in FIG. 1, constitutes a suspended membrane. Membrane 40' can be supported on a hard surface, such as capacitive sensing electrode 80 and substrate 100 by a variety of methods not shown in FIG. 4 that include: ultra thin viscous films, hydrophilic polymers, soft polymer cushions, aerogels, xerogels, and tethers. With this arrangement, there is no necessity to fabricate sensing volume 20, e.g., by etching a hole in silicon.

Figure 5:
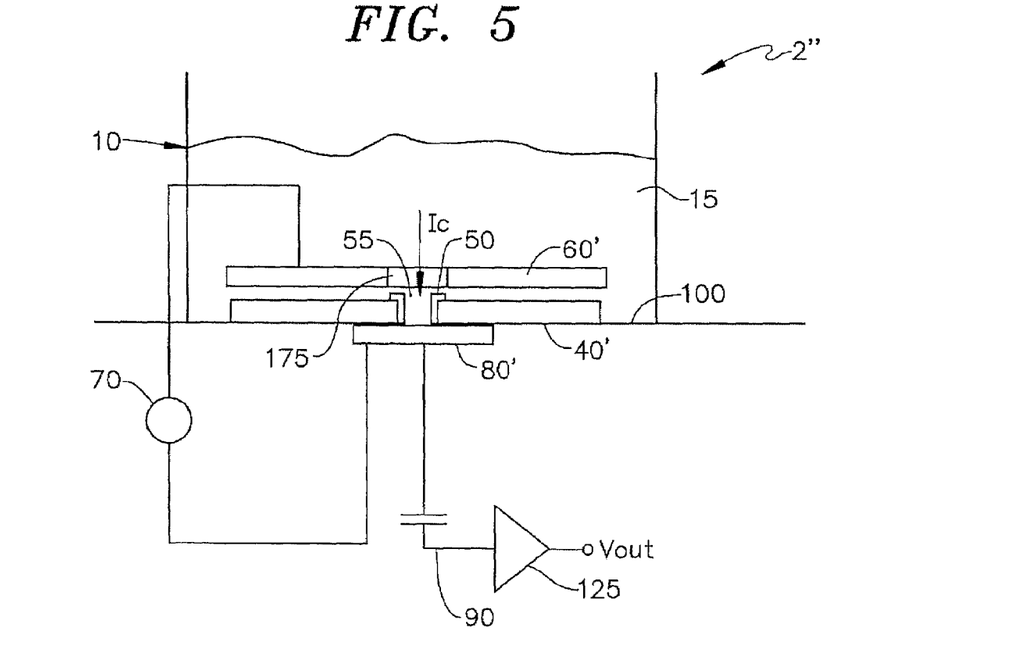
FIG. 5 is a schematic representation of a sensing system constructed in accordance with a third embodiment of the present invention.

In accordance with a third embodiment of the present invention as illustrated in FIG. 5, a sensing system 2" positions capacitive sensing electrode 80' near channel 50 either directly in contact or in the same manner as support membrane 40' shown in FIG. 4. First electrode 60' is positioned substantially closer to channel 50 in bath 10 and includes a hole 175 to allow the ionic current to enter channel 50. This geometry has the capability of measuring voltage variations directly across channel 50. Locating first electrode 60' so close to channel 50 (note electrode 60' could be atop membrane 40') requires depositing a material similar to that used to support membrane 40' and fabricating a conducting surface over that material. The presence of electrode 60' could be used to corral channel 50 in the desired region of membrane 40'. While technically challenging, the resulting embodiment of the invention enables the electric field across channel 50 to be measured directly.

In general, the present invention applies to any modulation of current $I_c$ in channel 50 such that it leads to a signal that can be measured. Particular applications of the invention are to measure discrete conductivity states in ion channels, protein pores, nanochannels and the like. These states can change stochastically in the presence of analytes in a manner that allows separate determination of concentration and species. The invention would preferably only utilize capacitive coupling to the electrolyte. With this arrangement, the DC potential is deduced from net ionic current flowing into the sensing volume. The required DC voltage is preferably maintained across channel 50 by driving bath voltage at a given potential difference from the measured sensing volume potential. Alternatively, allowing a specified amount of net charge to build up in sensing volume 20 and to bias the subsequent ion current $I_c$ to have zero average deviation about this net value creates a desired potential difference. The output waveform is then calculated based on capacitive coupling of the bias voltage to bath 10 and sensing volume 20. However, it should be noted that, although the patch clamp method employs a voltage clamp as disclosed, such a clamp is not required for all applications.

Another application of the invention is to measure channel current $I_c$ when conductivity is simply determined by a blocking effect produced by the presence of analyte 55 in an internal flow region of channel 50. Such a measurement constitutes the capacitive analog of the resistive pulse technique that is the basis of the Coulter counter. The capacitive technique has the same general benefits when going to smaller length scales as it does for stochastic sensing. Such a measurement of the ionic current $I_c$ has a number of new aspects and features that are of particular benefit in reducing the size of the apparatus used to make the measurement, and integrating an array of such an apparatus into a chip.

Although described with reference to a preferred embodiment of the invention, it should be readily understood that various changes and/or modifications could be made to the invention without departing from the spirit thereof. For instance, it should be readily apparent that multiple sensing systems could be incorporated into a single substrate or chip (not shown). Similarly, functionally identical versions of the sensing system built at different length scales, versions including different channels, membranes, electrode types, and electrode materials in any combination, can be integrated into a single chip. If provisions are taken to provide different discrete bath volumes, different electrolytes also can be used. In general, the invention is only intended to be limited by the scope of the following claims.

We claim:

1. An apparatus for sensing a time varying current passing through a channel provided in a membrane comprising:
   a membrane including a channel located therein;
   a voltage source for establishing a potential difference across the channel and driving an ionic current through the channel; and
   a capacitive sensing electrode positioned to measure an electrical property of the membrane.

2. The apparatus according to claim 1, further comprising:
   a bath; and
   a sensing volume separated from the bath by the membrane.

3. The apparatus according to claim 2, wherein the voltage source further comprises a first electrode located in the bath and a second electrode located in the sensing volume.

4. The apparatus according to claim 3, further comprising:
   a first electrolyte in the bath and a second electrolyte in the sensing volume, wherein the second electrode is capacitively coupled to the second electrolyte, with negligible contribution from resistive current.

5. The apparatus according to claim 2, wherein the voltage source comprises a first electrode located in the bath and the capacitive sensing electrode located in the sensing volume.

6. The apparatus according to claim 2, further comprising:
   means for adjusting an amplitude of a voltage of the voltage source to offset a build up of voltage in the sensing volume.

7. The apparatus according to claim 1, further comprising: circuitry, coupled to the capacitive sensing electrode, for determining the ionic current.

8. The apparatus according to claim 1, wherein the channel is selected from the group consisting of: an ion channel, a protein pore, a nanochannel and an engineered aperture.

9. The apparatus according to claim 1, wherein the channel has two defined conductive states.

10. The apparatus according to claim 1, wherein the membrane is formed from a bilipid or a liquid film.

11. The apparatus according to claim 1, wherein the membrane constitutes a solid.

12. The apparatus according to claim 11, wherein the membrane is formed from polycarbonate.

13. The apparatus according to claim 11, wherein the membrane is formed from polyimide.

14. The apparatus according to claim 1, wherein the sensing volume has a thickness less than approximately 1 mm.

15. The apparatus according to claim 1, wherein the sensing volume has a thickness less than approximately 1 µm.

16. The apparatus according to claim 1, wherein the sensing volume has a thickness less than approximately 10 nm.

17. The apparatus according to claim 1, further comprising:
a substrate wherein the membrane is supported on the substrate.

18. The apparatus according to claim 17, wherein the substrate is selected from the group consisting of: ultra thin viscous films, hydrophilic polymers, soft polymer cushions, aerogels, xerogels and tethers.

19. The apparatus according to claim 17, wherein the substrate constitutes a solid surface provided with a through hole.

20. The apparatus according to claim 17, wherein the voltage source further includes a first electrode located directly adjacent the channel opposite to the capacitive sensing electrode.

21. The apparatus according to claim 1, further comprising:
means for maintaining a driving voltage at a low level to minimize the ionic current passing through the channel.

22. The apparatus according to claim 1, further comprising:
means for producing a DC or quasi DC voltage across the channel by applying a driving current waveform with a net increasing signal over a desired time period.

23. A method of sensing a time varying current passing through a channel in a membrane located between a bath and a sensing volume comprising:
placing an analyte in the bath;
applying a driving voltage across the channel; and
measuring an electrical property of the membrane with a capacitive sensing electrode.

24. The method of claim 23, in which the channel switches between defined conductivity states in a stochastic manner.

25. The method of claim 23, further comprising: adjusting an amplitude of the voltage to offset a build up of voltage in the sensing volume.

26. The method of claim 23, further comprising: maintaining the driving voltage at a low level to minimize an ionic current passing through the channel.

27. The method of claim 23, further comprising: producing a DC or quasi DC voltage across the channel by applying a driving current waveform with a net increasing signal over a desired time period.

* * * * *